(12) United States Patent
Singer (10) Patent No.: US 9,186,315 B2
(45) Date of Patent: Nov. 17, 2015

(54) METHODS FOR DISGUISING DERMATOLOGICAL BLEMISHES

(75) Inventor: Matthew Singer, Memphis, TN (US)

(73) Assignee: Silicone Arts Laboratories, Inc., Memphis, TN (US)

( * ) Notice: Subject to any disclaimer, the term of this patent is extended or adjusted under 35 U.S.C. 154(b) by 387 days.

(21) Appl. No.: 13/444,426

(22) Filed: Apr. 11, 2012

(65) Prior Publication Data

US 2012/0192886 A1    Aug. 2, 2012

Related U.S. Application Data (60) Continuation-in-part of application No. 12/902,463, filed on Oct. 12, 2010, which is a division of application No. 11/765,790, filed on Jun. 20, 2007, now abandoned.

(51) Int. Cl.
| | |
|---|---|
| A45D 97/00 | (2011.01) |
| A45D 40/26 | (2006.01) |
| A61Q 90/00 | (2009.01) |
| A61K 8/89 | (2006.01) |
| A61Q 19/08 | (2006.01) |

(52) U.S. Cl.
CPC . *A61K 8/89* (2013.01); *A61Q 19/08* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 4,525,391 A | 6/1985 | Eckberg | |
| 4,538,920 A * | 9/1985 | Drake | 366/181.5 |
| 4,623,593 A | 11/1986 | Baier et al. | |
| 5,033,650 A * | 7/1991 | Colin et al. | 222/137 |
| 5,147,401 A | 9/1992 | Bakker et al. | |
| 5,333,760 A | 8/1994 | Simmen | |
| 5,336,014 A | 8/1994 | Keller | |
| 5,534,609 A * | 7/1996 | Lewis et al. | 528/15 |
| 5,722,829 A | 3/1998 | Wilcox et al. | |
| 5,895,794 A | 4/1999 | Berg et al. | |
| 5,922,314 A | 7/1999 | Hoang et al. | |
| 6,001,374 A | 12/1999 | Nichols | |
| 6,207,874 B1 | 3/2001 | Felton et al. | |
| 6,214,362 B1 | 4/2001 | Page | |
| 6,383,220 B1 | 5/2002 | van Blitterswijk et al. | |
| 7,189,384 B2 | 3/2007 | Halston et al. | |
| 7,241,009 B2 | 7/2007 | Kornfield et al. | |
| 7,316,795 B1 * | 1/2008 | Knauss | 264/313 |
| 2003/0187518 A1 | 10/2003 | Carls | |
| 2005/0100571 A1 | 5/2005 | Keyes | |
| 2005/0129649 A1 | 6/2005 | Kurosawa et al. | |
| 2005/0255300 A1* | 11/2005 | Funke et al. | 428/195.1 |
| 2006/0140896 A1 | 6/2006 | Decoster et al. | |
| 2006/0188850 A1* | 8/2006 | Mills | 434/100 |
| 2007/0212314 A1* | 9/2007 | Murphy et al. | 424/66 |

FOREIGN PATENT DOCUMENTS

| | | |
|---|---|---|
| WO | WO 2004/108175 | 12/2004 |
| WO | WO 2004108175 A1 * | 12/2004 |
| WO | WO 2006028612 A1 * | 3/2006 |

OTHER PUBLICATIONS

Over, Journal of Prosthodontics, 7, 4, 1998.*
Eggbeer, J Engineering in Medicine, 220, 2006.*
Lightspan Material Conversion, 2004.*
www.eagerplastics.com/siliconecolors.htm website (2 pages) (published between Jan. 1, 2001 and Jun. 5, 2007).
www.nusil.com/products/findproducts.
aspx?search=MED°0206820 website (6 pages) (published at least as of Jun. 5, 2007 and probably several years earlier.
D. Butler, G. Goin and R. Rupini, Silicone Auricular Prosthesis, J. of American Academy of Dermatologic Surgery, p. 687 (Oct. 2000).
M. Romanelli and V. Falanga, Use of a Durometer to Measure the Degree of Skin Induration in Lipodermatosclerosis, J. of Am. Academy of Derm., vol. 32. p. 188, (Feb. 1995).
www.danperezstudios.com/workshoppages/detail.htm website (10 pages) (Oct. 2001).
Converting a Two-part Lightspan Optical Gel or Thermoset to a One-part Material, Application Notes (May 24, 2004).
Office Action mailed Oct. 13, 2010 in related U.S. Appl. No. 11/765,790.
Office Action mailed Dec. 01, 2011 in related U.S. Appl. No. 11/765,790.
Office Action mailed Nov. 30, 2011 in related U.S. Appl. No. 12/902,463.
MED-6820 Optically Clear Silicone Elastomer, NuSil Silicone Technology (published Dec. 2006).
MED2-4220 Fast Cure Silicone Elastomer. NuSil Silicone Technology (Published Feb. 2008).
CV-1161 Controlled Volatility Pressure Sensitive Silicone Adhesive (Published Oct. 2009).

(Continued)

*Primary Examiner* — Susan Tran
*Assistant Examiner* — William Craigo
(74) *Attorney, Agent, or Firm* — Roberts Foster LLP (57) ABSTRACT

Methods for disguising dermatological blemishes are provided. The method includes providing a package containing at least a viscous silicone material and a catalyst. The silicone material or the catalyst is preferably tinted with a cosmetic pigment. The package may also include one or more dispensers, such as double-barrel syringes. The syringes hold the viscous silicone material and the catalyst, separately. The package may also have mixing tips through which the silicone material and the catalyst may be dispensed, whereupon the silicone material and the catalyst are mixed and applied to a user's skin for curing. The method includes applying the silicone mixture on a dermatological area of interest, applying one of the at least one skin texturing pad to the silicone mixture before the silicone mixture cures to create texture to the silicone material, and allowing the silicone material to cure on a skin surface of the human user.

24 Claims, 6 Drawing Sheets

(56) References Cited

OTHER PUBLICATIONS

Pages from www.dermaflage.com website owned by Applicant (or Applicant's comopany) (7 pages).
www.eagerplastics.com/rtvdil.htm (Eager Polymers article printed by examiner in Nov. 2011).
D. Eggbeer, et al., A Pilot Study in the Application of Texture, J. Engineering in Medicine, pp. 705-714 (2006).
L. Over, et al., Using a Colorimeter, J. of Prosthodontics, pp. 237-249 (1998).
Z. Khan, Materials Research in Maxillofacial Prosthetics, J. Dental Research, vol. 71 (1992).
Response to Office Action filed in related U.S. Appl. No. 12/902,463.
Screen shots taken from www.dermablend.com, accessed on Sep. 23, 2013.
Screen shots taken from www.sculptraaesthetic.com, accessed on Sep. 23, 2013.
Screen shots taken from www.juvederm.com, accessed on Sep. 23, 2013.

* cited by examiner

METHODS FOR DISGUISING DERMATOLOGICAL BLEMISHES

CROSS REFERENCE TO RELATED APPLICATIONS

This application is a continuation-in-part of and claims the benefit of U.S. Ser. No. 12/902,463 filed on Oct. 12, 2010. That application is entitled "A Cosmetic System and Method for Disguising Skin Defects."

The parent application was filed as a divisional of U.S. Ser. No. 11/765,790 filed 20 Jun. 2007 now abandoned, having the same title. Both applications are incorporated herein in their entireties by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

Field of the Invention

The present invention relates to cosmetic systems. More specifically, the invention relates to a cosmetic system that may be used to obscure dermatological defects. The invention also relates to methods for disguising dermatological blemishes.

Discussion of Technology

Some persons carry a skin defect that may cause embarrassment. The defect may be the result of a surgical procedure such as a tracheostomy, leaving permanent scarring in the neck. Alternatively, the defect may be a result of trauma such as an automobile accident, a fall, or an assault. Alternatively, the defect may be significant skin blemishes due to acne scarring. In any of these instances, the person may be self-conscious about their appearance and seek to disguise or camouflage the skin defect.

Cosmetic materials are well-known as a means of enhancing or otherwise altering a person's appearance. Cosmetics are used to cover inconsistent skin pigmentation and wrinkles. However, standard cosmetics are not always suitable where the skin defect is profound.

For significant physiological defects, prostheses such as maxillofacial prosthetics are known. Such prosthetics may be of particular use for patients who have undergone the removal of a highly visible portion of their anatomy such as an ear, the nose, or an ocular orbit due to cancer. U.S. Pat. No. 4,623,593 discusses such a prosthetic. The '593 patent is entitled "Self-Adhesive Polymer Composition for Use as Prosthetic Appliance," and discloses the use of polymeric materials for maxillofacial prosthetics.

The '593 patent notes that "[a] number of different types of polymeric materials have been utilized as base materials for prostheses." The patent mentions "silicone rubbers and polyurethanes." The '593 patent describes a molding process for the prosthetic that results in a tacky characteristic. The patent specifically states: "We have found that an integral surface layer having pressure-sensitive adhesive properties may be formed on an otherwise fully cured polymeric body. This may be accomplished by applying a sufficient amount of a cross-linking inhibition agent to selected surfaces of a mold cavity prior to packing the cavity with uncured monomeric, prepolymeric, or unvulcanized polymeric material. The mold is then closed and the material cured. The cross-linking inhibition agent acts on the surface or surfaces of the polymer to prevent complete cross-linking thereof. The body of the polymer is otherwise completely cured and has the same properties as would be expected." The end product is offered in a cured state.

Maxillofacial prosthetics may be too expensive or too cumbersome in the case of "mere" skin defects. U.S. Pat. No. 5,147,401 and U.S. Pat. No. 6,383,220 are each entitled "Artificial Skin." These patents teach skin coverings to aid in the protection and healing of flesh wounds. There is no discussion concerning the temporary covering of skin defects or scars, nor is there a teaching of applying an uncured or uncatalyzed silicone-based material to the patient's skin.

Therefore, a need exists for a cosmetic system that is able to disguise a profound skin defect such as surgical scarring or acne pitting that cannot be effectively covered by traditional makeup. Further, a need exists for a method of disguising dermatological blemishes using a cosmetic system that may be purchased by a consumer as a kit and used to create a translucent, realistic artificial skin in a dermatological area.

SUMMARY OF THE INVENTION

The present invention provides methods for disguising dermatological blemishes on a human user. The methods employ a cosmetic system in the form of a kit that is provided or sold to a user as a box or other package.

The method first includes opening the package. In one aspect, the package includes a first silicone container. Residing within the first silicone container is a viscous silicone material. The kit also includes a catalyst container. Residing within the catalyst container is a catalyst, such as a platinum metal catalyst. The catalyst is fabricated to react with the viscous silicone material such that when mixed with the silicone material and spread, the silicone material cures as a translucent elastic layer bonded to the human skin.

To facilitate bonding, the kit may include a skin prepping solution. The skin prepping solution may be, for example, a cleansing agent such as ethyl acetate. More preferably, the skin prepping solution may be a primer such as a silicone material dispersed in an alcohol. In this instance, the skin prepping solution may be rolled or brushed onto a user's skin.

The package also includes at least one skin texturing pad. The skin texturing pad is fabricated with dimples for creating texture to the translucent elastic layer while the silicone material is curing. In this way, dimples are formed in the elastic layer that reflect a porous pattern of a dermatological area of interest on the human user.

The elastic layer, when cured, is tinted. To enable this, the silicone material includes a pigment dispersed within the silicone material. Alternatively or in addition, the catalyst includes a pigment. The pigment is designed to tint the resulting elastic layer according to a selected skin tone.

In one aspect of the kit, a flocking agent is provided. The flocking agent is pre-mixed into the silicone material, the catalyst, or both. The flocking agent is designed to provide texture so that the elastic layer visually blends in with the user's skin. The flocking agent may comprise natural hair, natural fibers, or synthetic fibers.

The silicone container and the catalyst container may be separate jars from which a user can scoop a needed amount of material for mixing and curing. Alternatively, the catalyst and the base may reside in separate pump containers. More preferably, the silicone container and the catalyst container are cartridges or volumes that are held together in a dispenser. The dispenser may be either a dispensing gun or a syringe. In either instance, the double-barrel dispenser is used to extrude the silicone material and the catalyst together onto the user's skin from the silicone container and the catalyst container.

The cosmetic kit may further comprise a plurality of disposable mixing tips. Each tip is configured to removably attach to a distal end of the dispenser such that upon dispensing of the silicone material and the catalyst, a silicone mixture is formed that will quickly cure. Preferably, the silicone material and the catalyst are dispensed at substantially a 1:1 ratio by volume. As the viscous components are extruded through the tip of the volumes, the silicone material and the catalyst are mixed for curing on the user's skin.

The method also includes mixing a portion of the silicone material and a portion of the catalyst from the kit to form a silicone mixture. Preferably, the silicone material and the catalyst are extruded from a double-barrel syringe having a mixing tip. The method then includes applying the silicone mixture on a dermatological area of interest.

The method further includes applying one of the at least one skin texturing pad to the silicone mixture. This is done before the silicone mixture cures. In this way, texture is created along the silicone material. Thereafter, the method comprises allowing the silicone material to cure on a skin surface of the human user. The silicone mixture becomes removably bonded to the user's skin as it cures.

Other kits may be used with the method. For example, in an alternate embodiment the second cosmetic kit comprises a first syringe having a first and a second volume within a package. A viscous silicone material resides within the first volume. The silicone material is tinted to match a selected skin tone. Preferably, the silicone material is tinted by a pigment dispersed within the silicone material. The pigment may be a pigmented silicone oil, a pigmented cosmetic cream, or a pigmented powder.

The silicone material further has a flocking agent dispersed therein to provide texture. In this way the silicone material visually blends in to the user's skin upon curing.

A catalyst resides within the second volume. The catalyst is fabricated to react with the viscous silicone material such that when mixed with the silicone material, the silicone material cures as a translucent elastic layer capable of bonding onto human skin. Preferably, the dispenser is a double-barrel syringe that allows the silicone material and the catalyst to be extruded simultaneously in about a 1:1 volume ratio.

The alternate cosmetic kit also comprises a skin prepping solution. The kit may further have at least one skin texturing pad. The skin texturing pad is fabricated with dimples for creating texture to the translucent elastic layer while the silicone material is curing. In this way, dimples are formed in the elastic layer that reflect a porous pattern of a dermatological area of interest on the human user.

The alternate cosmetic kit also includes a box or other packaging. The box may contain at least the first syringe, the skin prepping solution, and the skin texturing pad. A plurality of disposable mixing tips may also be provided in the box. Each tip is configured to attach to a distal end of the syringe such that upon dispensing of the silicone material and catalyst, the silicone material and the catalyst pass through the mixing tip for mixing.

The alternate cosmetic kit may further comprise a second syringe and a third syringe. Each of the first, second, and third syringes has a first volume that contains a silicone material. The silicone material is tinted by a pigment, wherein the silicone material in each of the first, second and third syringes is tinted to match a different selected skin tone. In this way, a purchaser of the kit may readily choose a syringe that most closely matches his or her skin tone.

BRIEF DESCRIPTION OF THE DRAWINGS

So that the manner in which the recited features of the present invention can be better understood, certain drawings and/or flow charts are appended hereto. It is to be noted, however, that the appended artwork illustrates only selected embodiments of the inventions and are therefore not to be considered limiting of scope, for the inventions may admit to other equally effective embodiments and applications.

DESCRIPTION OF CERTAIN EMBODIMENTS

Definitions

As used herein, the term "flocking agent" refers to a collection of tiny spikes or hairs. The flocking agent may be fabricated from, for example, short natural or synthetic hair or fibers. The fibers are preferably colored.

The term "package" refers to any container that holds components for a cosmetic system. A package may be a small cardboard box or a box fabricated from other cellulosic material. Alternatively, the package may be fabricated from plastic or polycarbonate material.

The term "silicone material" refers to any viscous composition having a polymerized siloxane, or polysiloxane. Polysiloxanes have a silicon-oxygen backbone (Si—O—Si—O—Si—O . . . ) and an organic group (such as methyl, ethyl or phenyl) attached. The silicone material may be, for example, a linear silicone oil of the non-crosslinked polydimethylsiloxane (PDMS) type. Alternatively, the silicone material may be, for example, of the crosslinked organosiloxane type. The silicone material may be in the form of an emulsion. Suitable emulsions include but are not limited to water-in-silicone emulsions, oil-in-water emulsions, and silicone-in-water emulsions.

The term "catalyst" refers to a material which, when combined with silicone, cures to form a substantially solid material. A non-limiting example is a platinum-type catalyst.

The term "dispenser" refers to any apparatus that dispenses a silicone material and a catalyst in such a manner that the silicone material and the catalyst are available for mixing and curing. A non-limiting example is a double-barrel syringe that allows the materials to be simultaneously extruded and mixed.

Description of Selected Specific Embodiments

The present invention provides methods for disguising dermatological defects and blemishes. The methods employ a unique cosmetic system in the form of a kit that is provided or sold to a user in a box or package. The cosmetic system is a silicone-based system that can be used to temporarily fill acne blemishes. Alternatively, the cosmetic system may be used to disguise more significant scars that may arise from surgeries, diseases or traumatic accidents.

The cosmetic system first comprises a silicone material. In one embodiment, the silicone material is fabricated from a dimethyl silicone such as polydimethylsiloxane. Such silicones are available, for example, from NuSil Technology of Carpinteria, Calif. However, the cosmetic systems herein are not limited to any particular type or source of silicone material, so long as the silicone material may be catalyzed at room temperature. Preferably, the silicone material has the viscosity of a gel or soft solid at room temperature conditions, prior to catalysis.

It is necessary for the silicone material to be cured, such as through a process of catalysis. Therefore, the cosmetic system next includes a catalyst. The cosmetic systems herein are not any limited to any particular type or source of catalyst. However, it is preferred that a non-toxic reaction occur during catalysis. A preferred catalyst is a platinum metal catalyst.

One particularly desired combination of silicone material and catalyst is the NuSil™ MED2-4220. MED2-4220 comes in Parts A and B, with Part A being the catalyst, and Part B being the silicone material. For catalysis, Parts A and B of MED2-4220 may be degassed, and mixed at 50%/50% proportions. A 50 centistoke oil may be added to Part A, Part B, or both, prior to mixing. The oil serves as a diluent to facilitate extrusion through a dispenser (described below). Stated another way, the diluent reduces the viscosity of the silicone material. At higher percentages, the diluent also softens the final cured product, making it more pliable. This is of benefit for larger patch applications on a user's skin.

MED2-4220 provides an advantageous combination of silicone material and catalyst. Parts A and B each provide high viscosity and temperature tolerance before catalysis, and good optical clarity upon mixing and curing. It should be added that a small amount of platinum accelerator may optionally be added to the catalyst to accelerate the curing or vulcanization process. Accelerators may reduce the life of a resulting silicone product. However, the present application is designed to be temporary, i.e., lasting less than about 72 hours before it is removed.

The MED2-4220 NuSil™ product offers a fast-curing, medical grade, silicone elastomer. The elastomer cures with a translucent appearance in just about 5 minutes, and offers a tensile strength that is generally about 550 psi. Other NuSil™ products may be considered. For example, the MED-6820 combination of silicone material and catalyst may be advantageous in some contexts. MED-6820 offers a higher tensile strength, but may cure in too clear of a finish which may not be desired when covering dermatological blemishes.

As noted, the silicone material and the catalyst are mixed to provide a silicone mixture. In one aspect, the silicone mixture is custom-blended. This means that the mixture includes a cosmetic pigment that has been added to match a selected skin tone. Using pigments, various tints or shades of silicone mixture may be provided in different containers so that customers may select an intrinsically colored product that most closely matches their own skin tone.

The pigment is preferably a cosmetic pigment that is fabricated from a pressed cream. Examples of a suitable pressed cream include cream-based makeup. The cream may be water-based, silicone-based or petroleum-based.

As an alternative, the pigment may be a powder such as a cosmetic make-up powder. Alternatively, the pigment may be a silicone pigment. Various tones or colors of silicone pigment are available from NuSil Technology. Also, Eager Plastics, Inc. of Chicago, Ill. provides opaque silicone pigments having no/low odor and toxicity.

The pigment may be pre-mixed with the silicone material. Alternatively, the pigment may be pre-mixed with the catalyst, though preferably the pigment would not be a silicone-based cream in this instance. Alternatively still, the pigment may be supplied as a separate component and mixed with both the silicone material and the catalyst at the time the mixture is formed by a user. In this latter instance, the pigment will need a carrier material such as a low-viscosity silicone compound.

The cosmetic system optionally also includes a flocking agent. The flocking agent is used to provide depth and texture to the cosmetic mixture. The flocking agent may also provide color. Preferably, the flocking agent is pre-mixed with the silicone material. However, it may alternatively be pre-mixed with the catalyst. Alternatively still, the flocking agent may be supplied as a separate component with a pigment, and then mixed with both the silicone material and the catalyst at the time the mixture is formed by a user.

The flocking agent is preferably in the form of rayon fibers that are cut in very short sections, such as 5 to 25 mm. However, any material that is capable of providing texture to the silicone material may be used. Non-limiting examples include human hair, natural fibers, e.g., cotton and pulp, or synthetic fibers. The flocking agent may be of any color. However, in one aspect the flocking agent has a brown or black color so that flocking agent may be added to the silicone material to selectively darken the final mixture.

A very small amount of a thickening agent may be included with the silicone material. This is for the purpose of suspending the rayon fibers or other flocking agent in the viscous material. An example of a suitable thickening agent is the so-called Cabosil thickener. The term "cabosil" is an abbreviation for colloidal silica. Cabisol is a silica-based thickener that increases the viscosity of silicone. The silica-based thickener is desirable in the present application as it has been found that it will not change colors during the catalysis process. Cabosil is available from various sources, but is believed to be manufactured by Dow Chemical Company of Midland, Mich. and/or Cabot Corporation of Boston, Mass.

Another example of a thickening agent is a thixotropic agent. A thixatropic agent maintains a gel in a substantially solid or gelatinous phase during a sedentary state, but permits a reduction in viscosity when shaken or otherwise disturbed. The thixatropic agent also assists in suspending the rayon (or other) fibers. This prevents a condition known as "slumping."

Figure 1:
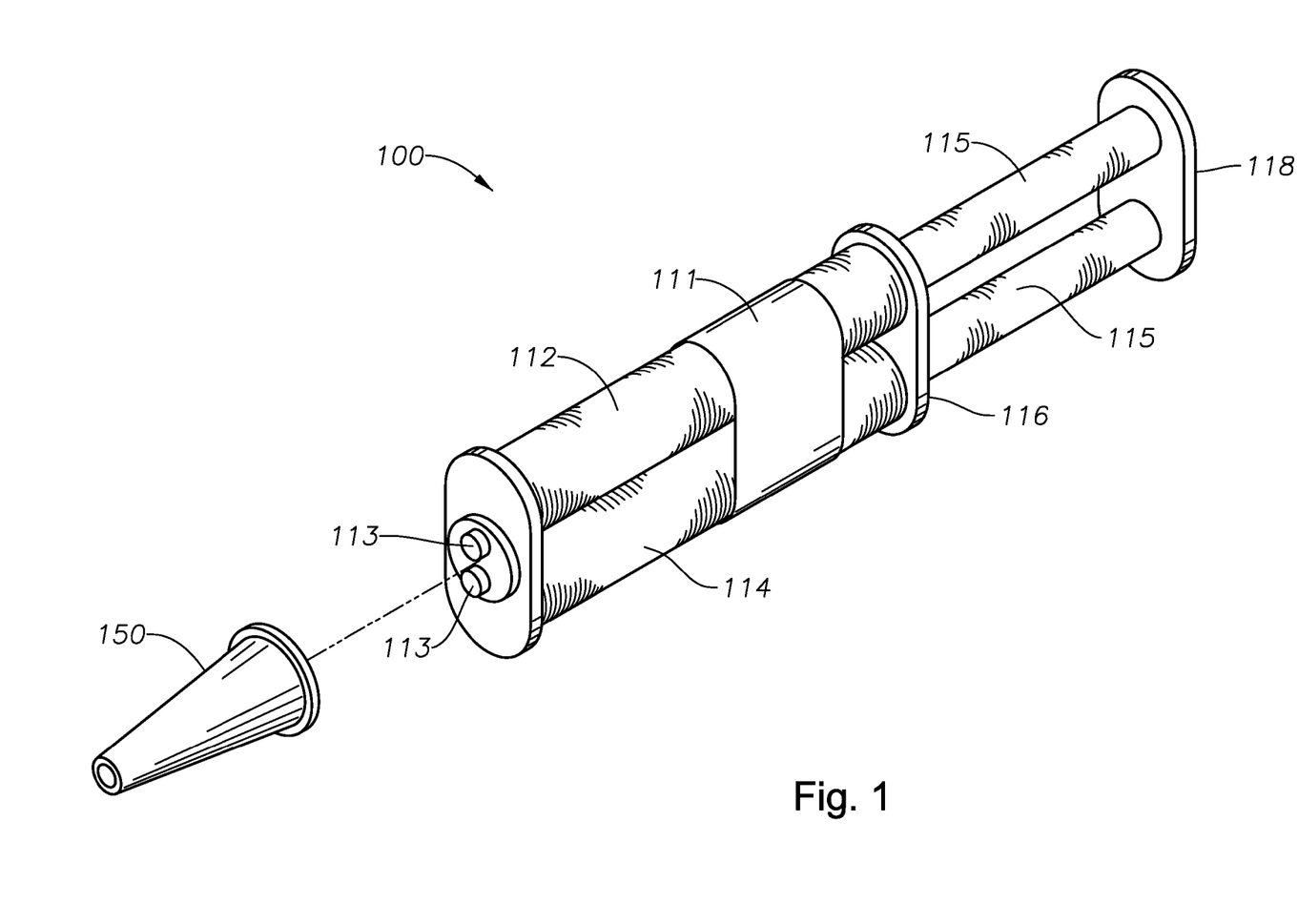
FIG. 1 is a perspective view of a syringe for dispensing a silicone material and a catalyst. A mixing tip is exploded away from the syringe for illustrative purposes. The syringe and mixing tip are used as part of the cosmetic system of the present invention, in one embodiment.

In order to dispense the silicone material onto a patient's skin, a dispenser is preferably employed. Thus, in one embodiment the cosmetic system includes a syringe. FIG. 1 is a perspective view of a syringe 100 for dispensing a silicone material and a catalyst together. The syringe 100 has a first volume 112 for containing a silicone material. The syringe 100 also has a second volume 114 for containing a catalyst. Thus, in the embodiment of FIG. 1, the syringe 100 is a double-barrel syringe.

Each volume 112, 114 terminates at a tip 113. The viscous silicone material and catalyst are extruded through respective tips 113. The materials may be extruded directly onto a human user's skin, or may be placed in a dish for manual mixing. Opposite the tips 113 is a base plate 116.

Each volume 112, 114 receives a plunger 118. A push-end 118 is provided at a proximal end of the plungers 118. In this way the user may push on the plungers 118 to simultaneously extrude the silicone material and the catalyst.

An optional mixing tip 150 may also be used as part of the syringe 100. The mixing tip 150 is detachable, and serves to mix the silicone material and the catalyst as the components are extruded from their respective volumes 112, 114. In the view of FIG. 1, the mixing tip 150 is exploded away from the syringe 100 for illustrative purposes.

The dispenser may alternatively be a dispensing gun. The dispensing gun is preferably a dual chamber applicator that receives two cartridges. A first cartridge holds the silicone material, while a second cartridge holds the catalyst.

In one aspect, the dispensing gun is the dispenser that was the subject of U.S. Pat. No. 5,333,760, entitled "Dispensing and Mixing Apparatus." The assignee of the '760 patent is listed as Coltene/Whaledent, Inc. of Mahwah, N.J. This patent is incorporated herein to the extent it is consistent with the present disclosure.

Figure 2:
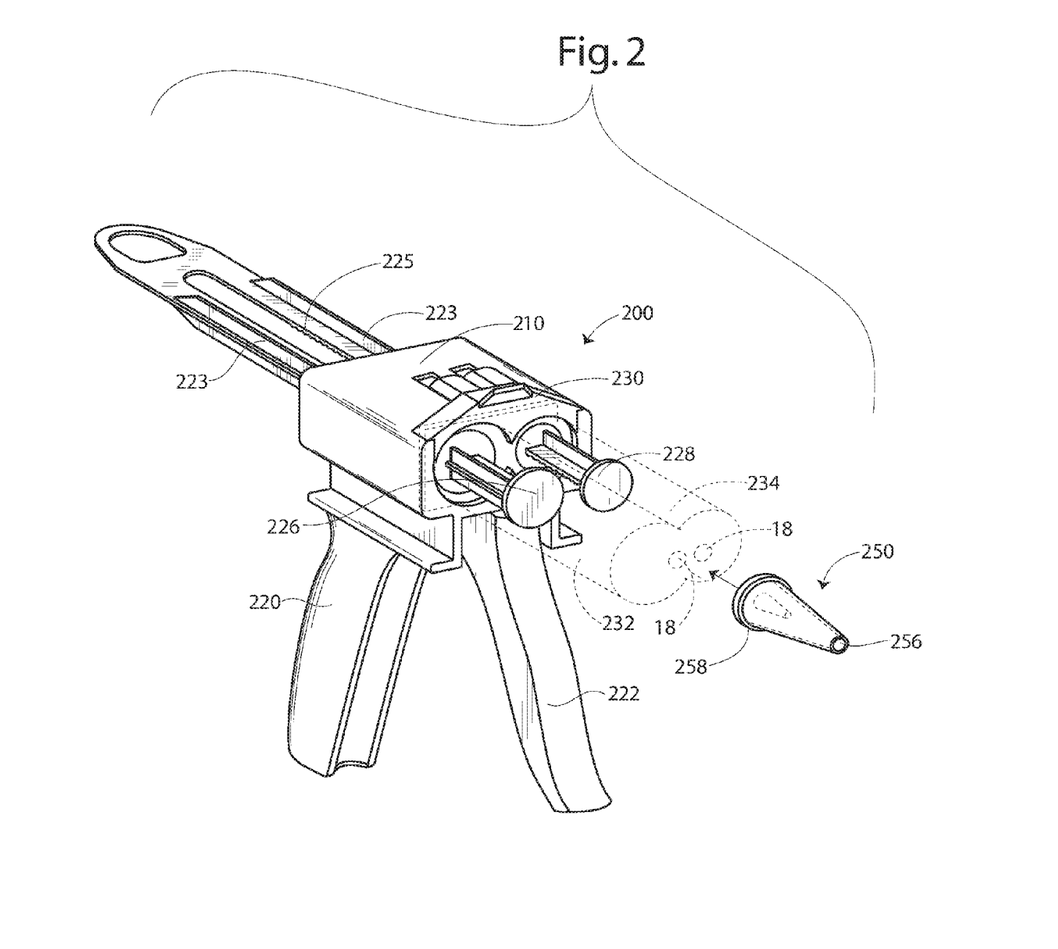
FIG. 2 is a perspective view of a dispensing gun as may be used as part of the cosmetic system of the present invention, in one embodiment. The dispensing gun is an alternative dispenser to the syringe of FIG. 1.

FIG. 2 provides a schematic view of another dispensing gun 200 as may be used in the cosmetic system herein. The illustrative gun 200 is a dual cartridge dispensing apparatus for dispensing and mixing the viscous components of the cosmetic system, to wit, the silicone material and the catalyst. The silicone material and the catalyst are held in respective cartridges. The cartridges are seen in phantom at 232 and 234, indicating that they are not part of the dispensing gun 200 itself. The first cartridge 232 is pre-packed with the silicone material, while the second cartridge 234 is pre-packed with the catalyst. Preferably, the silicone material in the first cartridge 232 is pre-mixed with the pigment, the flocking agent, and a thixatropic (or other thickening) agent.

As seen in FIG. 2, the dispensing gun 200 includes a body 210. The body 1210 supports other components of the dispensing gun 200 as described below. Operatively connected to the body 210 is a ratcheting system. The ratcheting system comprises a handle 220 and an actuating trigger 222. By repetitively squeezing the trigger 222, the silicone material and the catalyst are urged under pressure from the respective cartridges 232, 234 simultaneously.

The dispensing gun 200 also includes a chamber 230. The chamber 230 may be an elongated receptacle for receiving the cartridges, as in the dispensing apparatus of the '760 patent. In the '760 patent, the chamber is separated into two compartments, with each of the compartments receiving a separate cartridge in which the viscous components are stored. However, in the arrangement of FIG. 2 the chamber defines a slot. The slot 230 receives a plate (seen at 16 in FIG. 4) that in turn connects to and supports the two cartridges 232, 234.

The dispensing gun 200 also includes a pair of pistons 226, 228. The pistons 226, 228 act against the viscous materials in the cartridges 232, 234 in order to urge the materials from the cartridges 232, 234. Each of the pistons 226, 228 is carried at the end of a respective rail 223. The rails 223 travel forward through the body 210 and the chamber 230 of the dispensing gun 200 as the actuating trigger 222 is repetitively squeezed. The rails 223 include a toothed edge 225 which advances the pistons 226, 228 as part of the ratcheting system.

It is understood that the ratcheting system further includes gears, teeth or other advancing mechanism within the body. This commonly known feature is not illustrated or further described herein.

The dispensing gun 200 next includes a mixing tip 250. The use of a mixing tip, or "static mixer," is known in the art of mixing extruded components. The mixing tip may be of various types such as those described in U.S. Pat. Nos. 4,538,920; 3,923,288; 3,635,444, or others. In one arrangement, the mixing tip is integral to the chamber 230. This type of arrangement is shown in the dispensing apparatus of the '760 patent.

In the illustrative arrangement of FIG. 2, the mixing tip 250 defines a separate member. This means that the mixing tip 250 may be disconnected from other components for cleaning or even replacement. The mixing tip 250 includes a wall 254 and a central bore 255 (seen in FIG. 3) through which the viscous silicone material and the catalyst flow from the cartridges 232, 234, respectively, when the ratcheting system is actuated.

The mixing tip 250 of FIG. 2 includes a flanged proximate end 258. The flanged proximate end 258 is configured to snap into a bracket formed on the cartridges 232, 234. (The bracket is seen at 22 in FIG. 4 at the distal end 12 of the cartridges 232, 234.) In this way, a sealed connection between the cartridges 232, 234 and the mixing tip 250 may be acquired, while at the same time the mixing tip be removable and disposable.

The dispensing gun 200 will be provided to the user along with at least one cartridge 232 containing a tinted silicone material, and at least one cartridge 234 containing a catalyst. In addition, a plurality of disposable mixing tips 250 is preferably provided with the dispensing gun 100.

Figure 3:
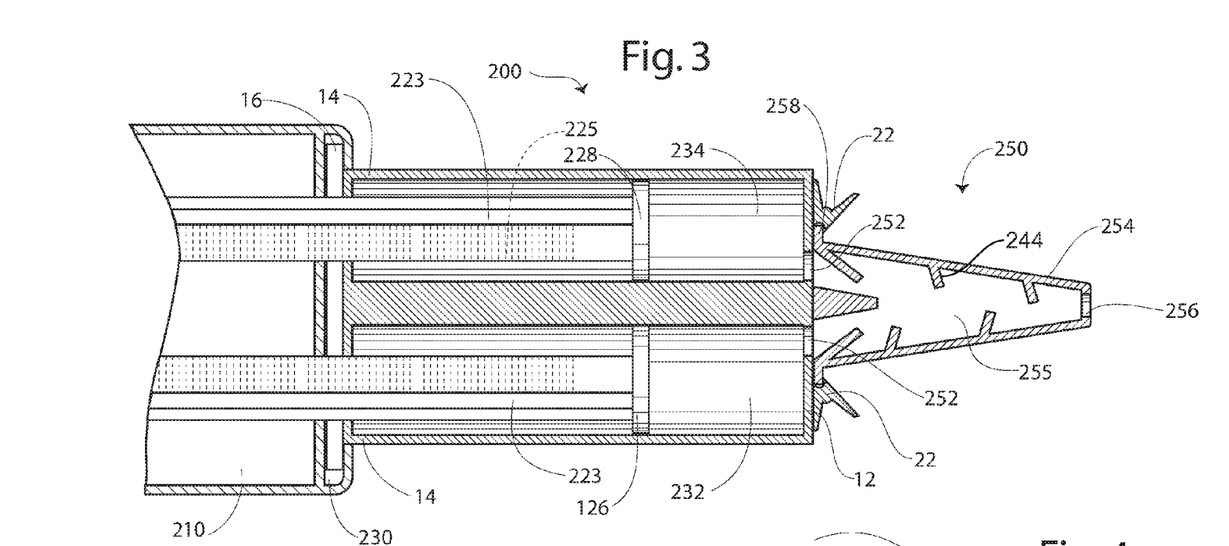
FIG. 3 is a top, cross-sectional view of a portion of the dispensing gun of FIG. 2.

FIG. 3 is a top, cross-sectional view of a portion of the dispensing gun 200 of FIG. 2. In this view, certain features of the dispensing gun 200 are more clearly seen. A portion of material in the cartridges 232, 234 has been extruded so that the rails 225 are visible. As noted, the rails advance through the body 210 in response to ratcheting of the trigger 222. Also visible is the slot 230. Again, the slot 230 receives the plate 16 that supports the cartridges 232, 234.

Also seen in FIG. 3 is a mixing tip 250. The mixing tip 250 is shown at the end of the rails 225. However, it is understood that the mixing tip 250 is actually connected to the distal ends 12 of the respective cartridges 232, 234, as described above.

The mixing tip 250 defines a central bore 255. The central bore 255 receives the viscous silicone material and the catalyst as they are urged from the dispensing gun 200 and the respective cartridges 232, 234. The viscous components are mixed as they travel through the bore 255. Preferably, the central bore 255 has a plurality of stationary mixing vanes 244 internal of the bore 255. The mixing vanes 244 can be of various shapes so long as they assist the components in being mixed together as they are forced through the bore 255.

Openings 252 are provided at the proximate flanged end 258 of the mixing tip 250. The openings 252 receive the viscous components as they are urged from the cartridges 232, 234. The components travel through the bore 255 and exit the mixing tip through a distal end 246.

Figure 4:
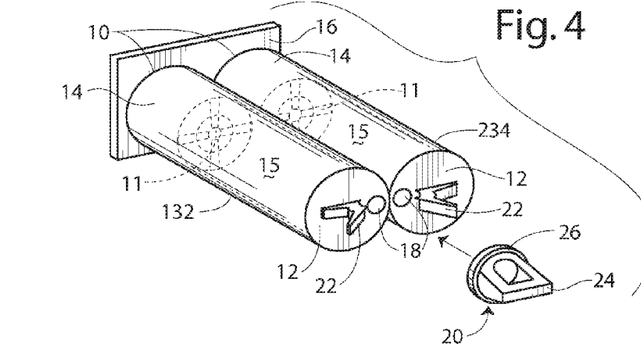
FIG. 4 is a perspective view of two cartridges or volumes for holding viscous liquids such as a silicone-based material and a catalyst.

FIG. 4 is a perspective view of two cartridges 232, 234 for holding the viscous components, to wit, the silicone-based material and the catalyst. The two cartridges 232, 234 are sized to be received within the chamber 230 of the dispensing gun 200. In the illustrative arrangement, the plate 16 slides into the slot that defines the chamber 230. The cartridges 232, 234 are preferably substantially circular in cross-section. Preferably, the cartridges 232, 234 are fabricated from a transparent or translucent plastic material.

Each cartridge 232, 234 defines an inner bore 15 or volume for receiving a viscous material. The diameter of the inner bore 15 may range from about 1.0 to about 3.0 cm, although this range is simply illustrative. The cartridges 232, 234 may have different inner diameters, or equivalent inner diameters. Each cartridge 232, 234 has a posterior end 10 and an anterior end 12. The posterior ends 10 each receive a sealed cap 11. The sealed cap 11 is movable along the inner bore 15 of the cartridges 232, 234 in response to force applied by the pistons 226, 228. The anterior ends 12 of the cartridges 232, 234 include an outlet 18. The outlets 18 in the cartridges 232, 234 are aligned with the openings 252 in the mixing tip 250.

The cartridges 232, 234 shown in FIG. 4 are integral. In this respect, the posterior ends 14 of the cartridges 232, 234 are connected to a plate 16. The plate 16, in turn, slides into the chamber 230 in the dispensing gun 200. The anterior ends 12 of the cartridges 232, 234 form a bracket 22. The bracket 22, in turn, receives a cap 20. The cap 20 slides into the opposing halves making up the bracket 22 in order to provide a seal to the openings 18 before the cartridges 232, 234 are loaded into the dispensing gun 200. The cap 20 includes a small handle 24 for gripping the cap 20.

When the dispensing gun 200 is ready for use, the cap 20 is removed from the cartridges 232, 234. The cartridges 232, 234 are then inserted into the slot defining the chamber 230. The mixing tip 250 is then slid into the bracket 22. In one aspect, the mixing tip 250 is rotated in order to lock the mixing tip 250 onto the bracket 22.

It is noted that the two cartridges 232, 234 may be separate items, that is, not permanently connected. It is also noted that more than two cartridges might be used in dispensing viscous fluids in the cosmetic system. For instance, a first cartridge might hold a silicone material, a second cartridge might hold a catalyst, and a third cartridge might hold a pigment in a carrier material. In this instance, the third cartridge would have a much smaller bore than the first and second cartridges. The flocking material may be included in any of the three cartridges or even all three.

The cartridges 232, 234 each contain a viscous component. The viscous components are extruded from the cartridges 232, 234 and through the openings 18 in response to action of the dispensing trigger 222. More specifically, the trigger 222 urges the pistons 226, 228, which in turn act against the sealed caps 11 at the posterior ends 10 of the cartridges 232, 234. Ultimately, the viscous components are extruded into the mixing tip 250 and out the distal end 246. In this way, the silicone material and the catalyst are mixed to form a silicone mixture so that a cosmetic material may be cured on the skin surface of a user. In one aspect, the cured silicone mixture has a durometer of about 5 to 25.

The dispensing guns 100, 200 shown and described in connection with FIGS. 1, 2 and 3 are merely illustrative. It is understood that any dispensing apparatus capable of moving the viscous components of the cosmetic system from a dispenser may be employed. Preferably, the silicone material and catalyst are mixed for application onto skin.

The cosmetic system may also comprise a skin prepping solution. In one embodiment, the skin prepping solution is designed to remove oil and dirt from a dermatological area of interest. For example, the skin prepping solution may be a solvent such as ethyl acetate. The skin prepping solution is applied to the skin before the silicone material is dispensed.

In another aspect, the skin prepping solution is a primer. An example of a primer is a silicone material dispersed in an alcohol. In this instance, the skin prepping solution may be rolled, brushed, or sprayed onto a user's skin. The user may wait 15 to 30 seconds after application. The alcohol flashes off, and a silicone film remains.

An example of a suitable primer is the CV-1161 from NuSil Silicone Technology of Carpentaria, Calif. CV-1161 is a translucent, pressure-sensitive, silicone adhesive. The applicant recommends that only a very light layer of CV-1161 ever be applied to skin, and that the primer never be inhaled or ingested.

After prepping, the silicone mixture may be applied to the patient's skin in different ways. First, the mixture may be applied directly to the skin as the mixture is extruded from the tips 113 of the dispenser 100. Alternatively, the mixture may be squeezed onto a dish (not shown) and then applied to the skin by use of a spatula (shown at 740 in FIG. 7) or other tool. Alternatively still, the mixture may be squeezed into the user's hand or into a dish, and then applied to the area of concern by hand. In any instance, the silicone mixture takes about 5 to 10 minutes to cure. Upon curing, the mixture constitutes a solid synthetic elastomer. Where a primer is used, the resulting translucent elastic layer will stay on the patient's skin for several days, even if the user takes a shower or goes swimming.

Figure 5A:
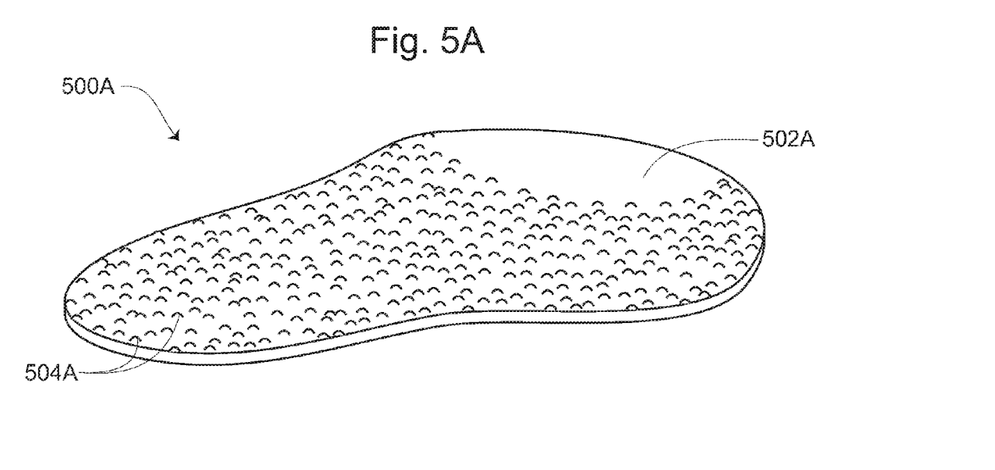
FIG. 5A is a perspective view of a skin-texturing pad as may be used in connection with the cosmetic system, in one embodiment.

The cosmetic system may also comprise a skin texturing pad. FIG. 5A presents an illustrative skin texturing pad 500A. The skin texturing pad 500A defines a thin, flexible substrate 502A having a plurality of dimples 504A. In the arrangement 500A, the dimples are large, and may be used to provide texture to a user's hand, arm, legs or foot, for example. Thus, the pad 500A has a texture designed to match the porous pattern of the dermatological area of interest.

Figure 5B:
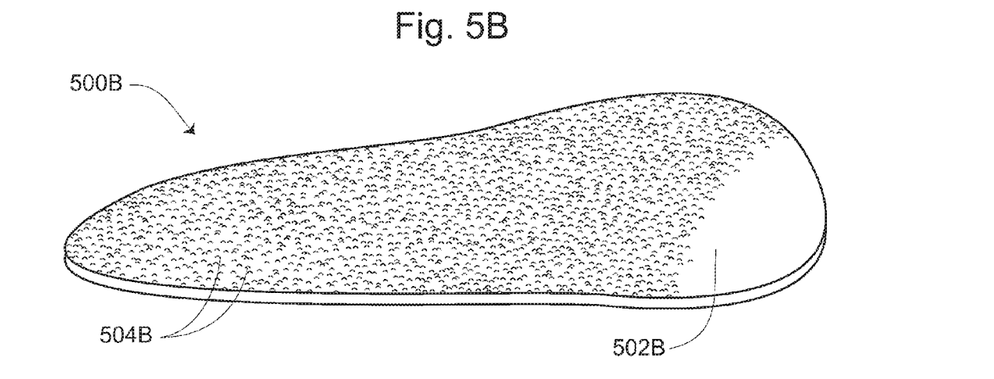
FIG. 5B is a perspective view of a skin-texturing pad in an alternate embodiment. The skin pad of FIG. 5 has finer features, and is designed to be used on the facial or neck areas of a user.

A separate skin texturing pad may be used on dermatological areas having finer features. FIG. 5B presents such a skin texturing pad 500B. The skin texturing pad 500B again defines a thin, flexible substrate 502B having a plurality of dimples 504B. However, in the arrangement 500B, the dimples are more subtle, and may be used to provide texture to a user's face, neck, or stomach, for example. In either instance, the use of a skin texturing pad 500A or 500B tends to reduce the shine or light reflection from the cured silicone material.

The pads 500A, 500B are preferably fabricated from urethane. Pads may optionally be acquired from Smooth-On, Inc. of Easton, Pa. After the pad 500A or 500B has been applied to the silicone, it is carefully removed. A matte skin cover disguising a dermatological blemish is left. The final material is dry to the touch, transparent, water resistant, durable, flexible, and has a natural texture. Under normal conditions it is anticipated that the dried material will last up to 72 hours.

Figure 6:
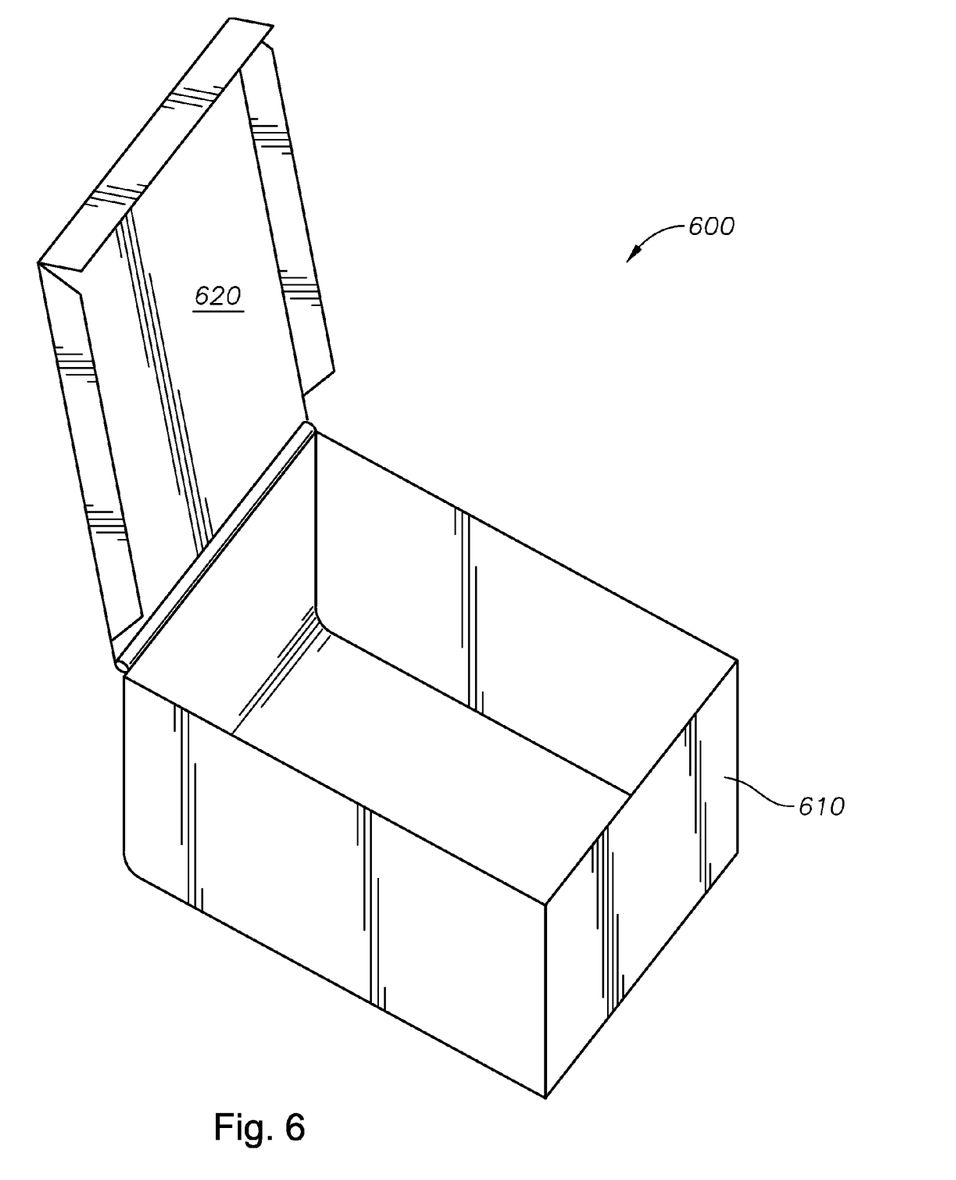
FIG. 6 is a perspective view of a box for containing components of a cosmetic kit for disguising dermatological blemishes on a human user, in one embodiment.

It is preferred that the components of the cosmetic system are provided or sold as a kit in a single package. The packaging is referred to herein as a box. An illustrative box is shown in FIG. 6 at 600. The box 600 includes walls 610 and a lid 620.

It is understood that the term "box" includes any form of suitably-sized packaging. A box is not limited to a traditional cardboard or plastic box having a lid, although such is preferred; instead, the term "box" may also include a blister pack or a bag.

In any aspect, the box 600 holds the various components making up the cosmetic system. These may include:

a dispenser (such as the syringe 100);
at least one volume or cartridge containing the silicone material (such as volume 112);
at least one volume or cartridge containing the catalyst material (such as volume 114);
a plurality of mixing tips (such as removable tip 150);
the skin prepping solution provided in a tube or bottle; and
one or more skin texturing pads, such as pads 500A, 500B.

Figure 7:
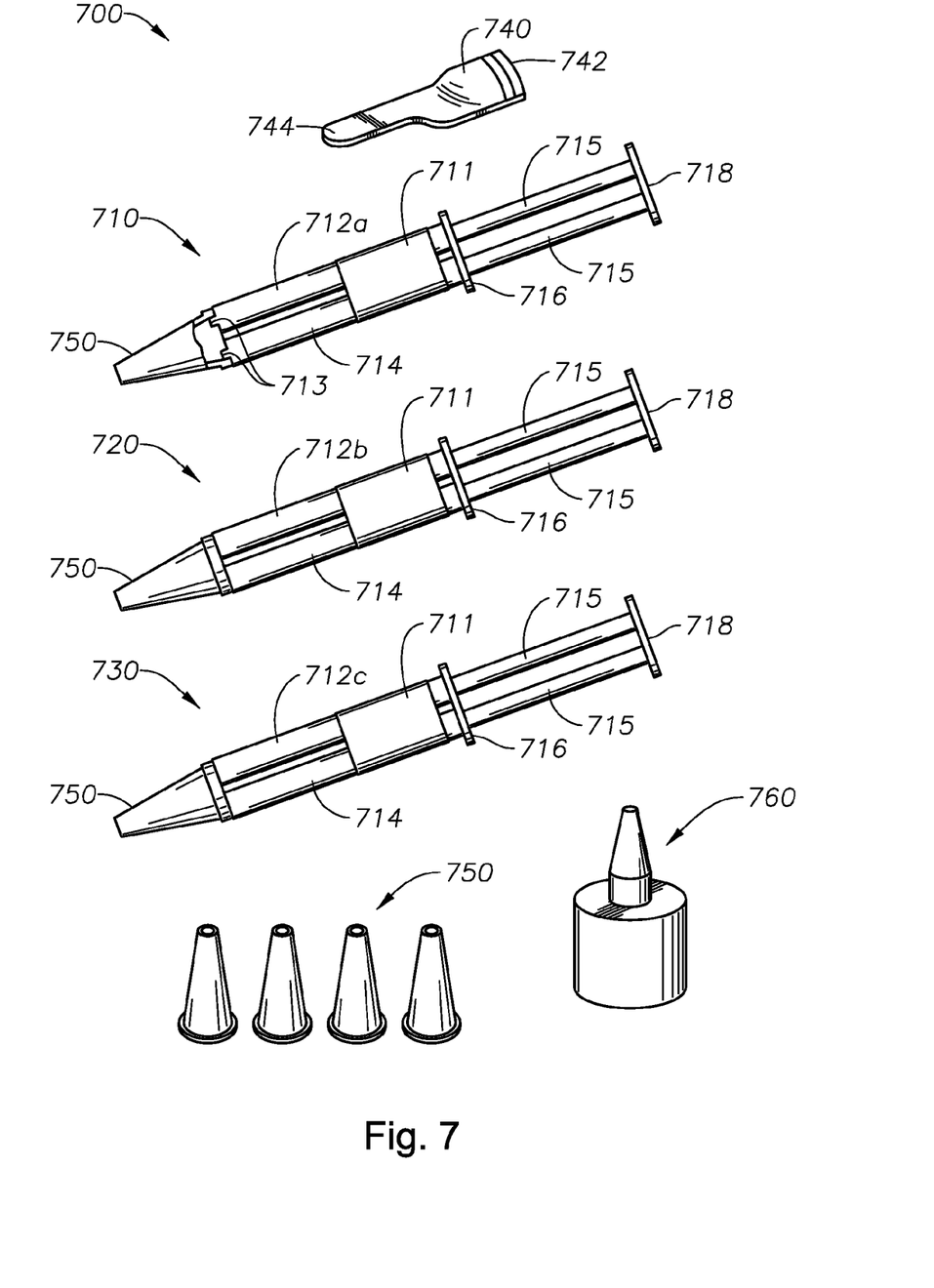
FIG. 7 is a collection of components that may be included in the box (or other package) of FIG. 6, for a cosmetic system.

FIG. 7 is a collection of components that may be included in the box 600 (or other package) of FIG. 6, for a cosmetic system. FIG. 7 first shows a set of three syringes 710, 720, 730. Each syringe 710, 712, 730 includes a pre-loaded volume containing a tinted silicone material. Volume 712a is tinted to match a first selected skin tone; volume 712b is tinted to match a second selected skin tone; and volume 712c is tinted to match a third selected skin tone. In this way, the user may experiment with the different syringes 710, 720, 730 to determine which one most closely approximates their own skin tone. Preferably, the box 600 will include three or even more sets of cartridges containing the viscous silicone material.

Each syringe 710, 712, 730 will also include a volume containing a catalyst. This is shown at 714. The volumes 712, 714 then each have a nozzle 713 through which viscous material is extruded, and a plunger 715. A band 711 and a plate 716 connect the cartridges 712, 714 together, along with a push-end 718.

FIG. 7 also shows a spatula 740. The illustrative spatula 740 has a body 742 by which the spatula 740 is held. The spatula 740 also has a tip 744 for further mixing a silicone-catalyst mixture and applying the mixture onto the user's skin. Preferably, a cosmetic kit will have two or more spatulas 740.

FIG. 7 also shows a mixing tip 750. More specifically, several disposable mixing tips 750 are shown. These removably attach to the tip of the dispensing gun or to the tips of the cartridges 712, 714 to cover the nozzles 713.

Finally, FIG. 7 shows a bottle 760. The illustrative bottle 760 holds a skin prep solution. It is understood that the skin-prep solution may alternatively be held in pre-soaked wipes or tubes (not shown).

Based on the above-described cosmetic system and components, a method is provided herein for disguising dermatological blemishes on a human user. In one aspect, the method includes providing a package containing a cosmetic system. Generally, the system will include a viscous silicone material and a catalyst. The silicone material, the catalyst, or both is preferably tinted with a pigment according to a desired skin tone. In one aspect, the cosmetic system also includes a flocking agent. The flocking agent is pre-mixed with the silicone material or the catalyst (or both) to provide texture.

The package may also have at least one skin texturing pad. The skin texturing pads are textured in accordance with the dermatological area of interest. Ideally, the pads are created from molds that, in turn, have been created from impressions taken on actual physical skin.

The method also includes mixing a portion of the silicone material and a portion of the catalyst to form a silicone mixture. Preferably, the silicone material and the catalyst are simultaneously extruded from a dispenser. A removable and disposable mixing tip is provided through which the silicone material and the catalyst may be dispensed, whereupon the silicone material and the catalyst are mixed for curing. The viscous mixture of silicone material and catalyst is applied to a dermatological area of interest, either directly onto the user's skin or by using a tool such as a small spatula.

In one aspect, the method also includes applying one of the at least one skin texturing pads to the silicone mixture before the silicone mixture cures. This creates texture to the silicone material. The method may include selecting a particular texturing pad having dimples to match a skin pattern of the dermatological area of interest.

Using the texture pads, a user is able to impart texture to the silicone mixture to the mixture before it cures. In this way, the mixture creates a seamless blend between the defect site and the surrounding flesh as it cures. Even the non-artist can obtain a nice blend into the skin with little to no training. The skin texturing pad is then removed from the user's skin before the silicone mixture fully cures.

The method then includes allowing the silicone material to cure on a skin surface of the human user. The silicone mixture becomes bonded to the user's skin.

The package may optionally have a skin prepping solution. The method then includes the step of applying the skin prepping solution to the dermatological area of interest. The skin prepping solution is applied prior to applying the silicone material to the dermatological area of interest. In one aspect, the skin preparation creates a thin film of silicone that enables the silicone material from the dispenser to stick firmly to the skin. In another aspect, the prepping material helps to remove any oils or dirt that may be present on the skin which may interfere with adhesion. A cotton ball or cloth may be used for wiping the skin with the prepping solution.

In this method, it is preferred that the silicone material and the catalyst are provided in separate but connected volumes of a syringe. Preferably, the volumes are sized such that the silicone material and the catalyst are dispensed in substantially a 1:1 volume ratio. In one aspect, the user selects from a first syringe, a second syringe, and a third syringe in a package, wherein each of the first, second, and third syringes has a silicone material that is tinted according to a selected skin tone. Each of the first, second, and third syringes includes a volume of catalyst material. In this way, the user may create a cured, translucent covering that is tinted most closely according to their skin.

In one aspect, the user chooses a set of syringes from three or more different sets of syringes. For example, a first set of syringes may be tinted for Caucasian skin tones, a second set of syringes may be tinted for ethnic skin tones, and a third set of syringes may be tinted for Asian skin tones. Each of the three sets, in turn, has three or more syringes offering light, medium and dark tints. Thus, the user may select a package containing either Caucasian, ethnic, or Asian skin tones, and then within that package select from the light, medium or dark tinted syringes. The patient selects the "kit" that most closely matches his or her skin tone.

The method may also include applying facial makeup to the dermatological area of interest prior to applying the silicone mixture to the dermatological area of interest. It is noted that the silicone material dries translucently, and additional makeup need not be placed over the silicone material. However, it is also within the scope of the present disclosure to provide a silicone-based makeup that covers over the cured elastic silicone layer. The custom blend of the silicone material, the catalyst and the pigment is preferably designed so that an element of translucence is maintained. Ideally, the cured silicone mixture should not interfere with the user's skin appearance, but should blend in so as not to be notice. However, in some instances a user may have a scar that has left a different skin coloration than their natural skin. In this instance, the user may choose to use a special makeup that blends in the color of the scar tissue with the surrounding skin.

Ancillary to the cosmetic system is a consideration as to pigmentation for users in the market place. The human race presents a true "kaleidoscope" of colors. In one aspect, it is desirable to select a minimum number of pre-mixed syringes which nevertheless support the "skin kaleidoscope" presented by the marketplace. In another aspect, it is desirable to offer a color-matching system wherein a silicone material is custom blended specifically for an individual user by using a computer-driven color matching system.

The foregoing description and examples have been set forth merely to illustrate the inventions herein and are not intended to be limiting. Since modifications of the disclosed embodiments incorporating the spirit and substance of the inventions may occur to persons skilled in the art after reading this disclosure, the inventions should be construed broadly to include all variations falling within the scope of the appended claims and equivalents thereof.

For example, it is within the spirit and scope of the present invention to dispense and mix the silicone material and the catalyst manually. The silicone material and the catalyst may be provided as part of a cosmetic system in separate jars or bottles or in separate pump containers. The jars may be sold, for example, in a bundled manner, or sold separately. In any event, the silicone material and the catalyst are preferably mixed at substantially a 1:1 ratio by volume in order to form the silicone mixture.

What is claimed is:

1. A method for disguising dermatological blemishes on a human user, comprising:
    determining a tone of the user's skin;
    opening a package containing at least:
        a silicone container;
        a viscous silicone material within the first silicone container; a catalyst container;
        a catalyst within the catalyst container, wherein the catalyst is fabricated to react with the viscous silicone material such that when mixed with the silicone material, the silicone material cures as a translucent elastic layer capable of bonding onto human skin; and
        at least one skin texturing pad fabricated from a mold, the at least one skin texturing pad having dimples for creating texture to the translucent elastic layer such that the dimples reflect a porous pattern of a dermatological area of interest on the human user, wherein:
        (i) the silicone material is tinted by a pigment dispersed within the silicone material, (ii) the catalyst is tinted by a pigment dispersed with the catalyst, or (iii) both; and
        the pigment is designed to tint the elastic layer according to the user's skin tone;
    mixing a portion of the silicone material and a portion of the catalyst to form a silicone mixture;
    applying the silicone mixture on the dermatological area of interest to fill the dermatological blemish;
    applying one of the at least one skin texturing pad to the silicone mixture on the dermatological blemish before the silicone mixture cures to create texture to the silicone material;
    removing the at least one skin texturing pad from the dermatological blemish after texturing has been created but within about five minutes; and
    allowing the silicone material to cure on the dermatological area of interest of the human user, wherein the translucent elastic layer becomes bonded to the user's skin.

2. The method of claim 1, wherein:
    (i) the silicone material contains a flocking agent, (ii) the catalyst contains a flocking agent, or (iii) both; and
    the flocking agent is designed to provide texture so that the elastic layer visually blends in with the user's skin upon application.

3. The method of claim 2, wherein:
    the flocking agent resides within the silicone material;
    the flocking agent comprises natural hair, natural fibers, or synthetic fibers; and
    the silicone material further comprises a thixotropic agent, a thickener, or both for suspending the natural hair, natural fibers, or synthetic fibers.

4. The method of claim 1, wherein the silicone container and the catalyst container comprise separate jars or separate containers having pumps.

5. The method of claim 1, wherein:
    the silicone container is a cartridge configured to be loaded into a dispensing gun;
    the catalyst container is a cartridge also configured to be loaded into a dispensing gun; and
    the method further comprises loading the cartridges into the dispensing gun.

6. The method of claim 5, wherein the package further comprises:
    a plurality of disposable mixing tips, with each tip being configured to attach at a distal end of the silicone container and the catalyst container such that upon dispensing of the silicone material and catalyst, the silicone material and the catalyst pass through the mixing tip for mixing.

7. The method of claim 1, wherein:
    the silicone container and the catalyst container are connected to form a first double-barrel syringe; and
    mixing a portion of the silicone material and a portion of the catalyst to form a silicone mixture comprises extruding the silicone material and extruding the catalyst together from the double-barrel syringe.

8. The method of claim 7, wherein the package further comprises:
    a plurality of disposable mixing tips, with each tip being configured to removably attach to a distal end of the first syringe such that upon dispensing of the silicone material and the catalyst, the silicone material and the catalyst pass through a mixing tip for mixing; and
    the method further comprises attaching one of the plurality of mixing tips to a distal end of the double-barrel syringe; and
    mixing a portion of the silicone material and a portion of the catalyst further comprises extruding the silicone material and extruding the catalyst together through the mixing tip.

9. The method of claim 7, wherein:
    the silicone material in the first syringe is tinted according to a first selected skin tone; and
    the package further comprises at least a second syringe and a third syringe also having separate volumes of silicone material and catalyst, with the silicone material in the second and third syringes being tinted according to second and third selected skin tones, respectively.

10. The method of claim 1, wherein the package comprises a box having a lid.

11. The method of claim 1, wherein:
the package further comprises a skin prepping solution; and
the method further comprises applying the skin prepping solution to the dermatological area of interest prior to applying the silicone mixture to the user's skin.

12. The method of claim 11, wherein the skin prepping solution comprises a silicone material within a dispersant, with the skin prepping solution being fabricated to cause the silicone mixture to temporarily bond to the human user's skin.

13. A method for disguising dermatological blemishes on a human user, comprising:
opening a package containing at least:
a first syringe having at least a first volume and a second volume;
a viscous silicone material within the first volume, the silicone material being tinted to match a selected skin tone and having a flocking agent dispersed therein to provide texture so as to visually blend in to the user's skin;
a catalyst within the second volume, wherein the catalyst is fabricated to react with the viscous silicone material such that when mixed with the silicone material, the silicone mixture cures as a translucent elastic layer capable of bonding onto human skin;
a skin prepping solution comprising a dispersed silicone material; and
at least one skin texturing pad fabricated from a mold, the skin texturing pad being designed with dimples for creating texture to the translucent elastic layer such that the dimples generally reflect a porous pattern of a dermatological area of interest on the human user;
determining a tone of the user's skin;
applying a portion of the skin prepping solution to the dermatological area of interest;
extruding a portion of the silicone material and a portion of the catalyst from the syringe as a silicone mixture;
applying the silicone mixture on the dermatological area of interest to fill the dermatological blemish;
applying one of the at least one skin texturing pad to the silicone mixture on the dermatological blemish before the silicone mixture cures to create texture to the silicone material over the dermatological area of interest and to seamlessly blend with the user's skin;
removing the at least one skin texturing pad from the dermatological blemish after texturing has been created but within about five minutes; and
allowing the silicone mixture to cure on the dermatological area of interest of the human user, wherein the silicone mixture becomes bonded to the user's skin.

14. The method of claim 13, wherein the silicone material in the first syringe further comprises a thickening agent for suspending the flocking agent.

15. The method of claim 13, wherein:
the package further contains a plurality of disposable mixing tips, with each tip being configured to reside proximate a distal end of the first syringe such that upon dispensing of the silicone material and catalyst, the silicone material and the catalyst pass through the mixing tip for mixing; and
the method further comprises attaching one of the plurality of mixing tips to an end of the double-barrel syringe.

16. The method of claim 15, wherein: the package further comprises:
a second syringe and a third syringe, wherein each of the first, second, and third syringes has a first volume containing a viscous silicone material, and a second volume containing a catalyst, and the silicone material in each of the first volumes is tinted by a pigment dispersed within the silicone material, wherein the silicone material in each of the first, second and third syringes is tinted to match a different selected skin tone; and
the method further comprises selecting a syringe that best matches the skin tone of the user.

17. The method of claim 13, wherein the first and second volumes are sized such that the silicone material and the catalyst are dispensed from the first syringe in substantially a 1:1 volume ratio.

18. The method of claim 13, wherein:
the silicone material comprises a platinum, RTV silicone material; and the catalyst comprises a platinum metal catalyst.

19. The method of claim 13, wherein:
the at least one skin texturing pad comprises two separate skin texturing pads, with each of the at least two skin texturing pads having a different dimple pattern; and
the method further comprises selecting a skin texturing pad to match a skin pattern of the dermatological area of interest.

20. A method for disguising dermatological blemishes on a human user, the method comprising:
determining a tone of the user's skin;
accessing a cosmetic kit comprising:
a first syringe having a first volume and a second volume;
a first viscous silicone material pre-loaded within the first volume, with the first silicone material being tinted to match a first skin tone;
a second syringe also having a first volume and a second volume;
a second viscous silicone material pre-loaded within the second syringe, with the second silicone material being tinted to match a second selected skin tone that is different than the first selected skin tone;
a catalyst pre-loaded within the second volume of each of the first and second syringes, the catalyst having a flocking agent dispersed therein to provide texture so as to visually blend in to a user's skin, and wherein the catalyst is fabricated to react with the first or second viscous silicone material such that when mixed with the first or second silicone material, the silicone mixture cures as a thin, translucent elastic layer that bonds onto human skin;
a plurality of disposable mixing tips, with each tip being configured to removably attach to a distal end of the first and second respective syringes, and to mix the first or second silicone material with the catalyst as the first or second silicone material and the catalyst are extruded from the first or second syringe;
a skin prepping solution comprising a silicone material dispersed within an alcohol;
at least one skin texturing pad fabricated from a mold, the skin texturing pad being designed with a dimple pattern for creating texture to the translucent elastic layer before it cures such that the dimples generally resemble the porous pattern of a dermatological area of interest on the human user; and
a box containing at least the first and second syringes, the plurality of disposable mixing tips, the skin prepping solution, and the skin texturing pad;
applying a portion of the skin prepping solution to the dermatological area of interest as a primer;

selecting a syringe having a viscous silicone material that most closely matches the user's skin tone;

extruding a portion of the silicone material and a portion of the catalyst from the selected syringe as a silicone mixture;

applying the silicone mixture on the dermatological area of interest to fill the dermatological blemish;

applying one of the at least one skin texturing pad to the silicone mixture on the dermatological blemish before the silicone mixture cures to create texture to the silicone mixture over the dermatological area of interest and seamlessly blends with the user's skin;

removing the at least one skin texturing pad from the dermatological blemish after texturing has been created but within about five minutes; and allowing the silicone mixture to cure on the dermatological area of interest of the human user, wherein the textured elastic layer becomes bonded to the user's skin.

21. The method of claim 20, wherein the package further comprises: a third syringe having a first volume and a second volume;

a third viscous silicone material within the first volume of the third syringe, the third silicone material being tinted by a pigment dispersed within the silicone material, with the third silicone material being tinted to match a third selected skin tone that is different from the first and second selected skin tones; and a catalyst within the second volume of the third syringe.

22. The method of claim 20, further comprising:
selecting a texturing pad having a dimple pattern that most closely matches the porous pattern of the dermatological area of interest.

23. The method of claim 20, further comprising:
applying facial makeup to the dermatological area of interest prior to applying the silicone mixture to the dermatological area of interest.

24. A method for disguising dermatological blemishes on a human user, comprising:

determining a tone of the user's skin;

combining a viscous silicone material tinted to match the tone of said user's skin with a catalyst, wherein the catalyst is fabricated to react with the silicone material such that when mixed with the silicone material, the silicone mixture cures as a translucent elastic layer capable of bonding onto human skin;

applying the silicone mixture on the dermatological area of interest to fill the dermatological blemish;

applying a skin texturing pad to the silicone mixture on the dermatological blemish before the silicone mixture cures to create texture to the silicone material over the dermatological area of interest and to seamlessly blend with the user's skin;

removing the at least one skin texturing pad from the dermatological blemish after texturing has been created but within about five minutes; and allowing the silicone mixture to cure on the dermatological area of interest of the human user, wherein the silicone mixture becomes bonded to the user's skin.

* * * * *